US00PP20618P2

(12) United States Plant Patent
Ui

(10) Patent No.: US PP20,618 P2
(45) Date of Patent: Dec. 29, 2009

(54) ***CALIBRACHOA* PLANT NAMED 'SAKCAL097'**

(50) Latin Name: ***Calibrachoa* sp.**
Varietal Denomination: Sakcal097

(75) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/286,274

(22) Filed: Sep. 29, 2008

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L Bell
(74) *Attorney, Agent, or Firm*—Jondle & Associates, P.C.

(57) ABSTRACT

'SAKCAL097' is a new *Calibrachoa* cultivar particularly distinguished by having blue flowers, a large flower size and a creeping growth habit, is disclosed.

1 Drawing Sheet

Figure 1:
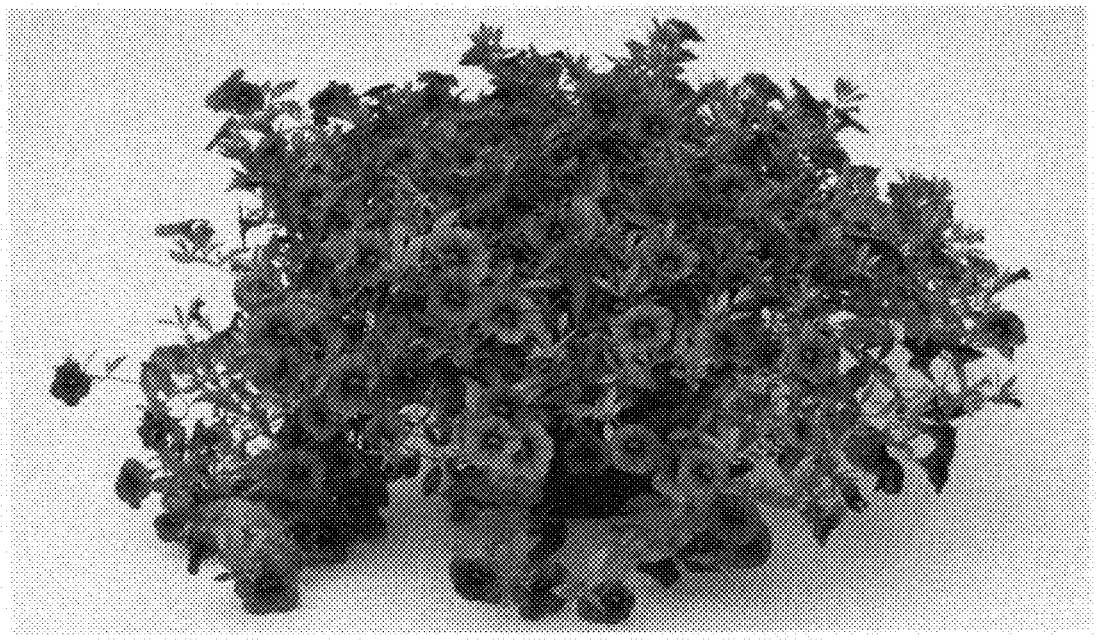

Genus and species: *Calibrachoa* sp.
Variety denomination: 'SAKCAL097'.

BACKGROUND OF THE INVENTION

The present invention comprises a new and distinct cultivar of *Calibrachoa*, botanically known as *Calibrachoa* sp., and hereinafter referred to by the cultivar name 'SAKCAL097.' It is characterized by having blue flowers, large flower diameter and creeping plant and growth habit. 'SAKCAL097' originated from a hybridization made in 2001 in Kakegawa, Japan. The female grandparent was a proprietary hybrid *Calibrachoa* breeding line named '0BC-13A' (unpatented) and had a carmine-rose flower color, large flower size and a semi-mounding plant and growth habit. The male grandparent was a proprietary hybrid *Calibrachoa* breeding line named '9B-74AA-1' (unpatented) characterized by its violet flower color and creeping plant and growth habit.

In February 2001, '0BC-13A' and '9B-74AA-1' were crossed and seeds were obtained. In February 2001, the $F_1$ seed was sown in the greenhouse, cultivated and plant lines were produced with mounding plant habit and creeping plant habit. Three plant lines were selected within the $F_1$ plants that had rose colored flowers and a creeping plant growth habit. The three plant lines were intercrossed. The exact female and male parentage is unknown.

In August 2001, seeds obtained were sown in the greenhouse, cultivated and plant lines were produced with flower colors of rose and blue, each with a creeping plant habit. The line 'K2-125' was selected for its blue flower color, large flower size and creeping plant growth habit.

In February 2002, line 'K2-125' was vegetatively propagated by cuttings, cultivated and evaluated.

In April 2002, line 'K2-125' was confirmed to be fixed and stable. Line 'K2-125' was propagated again in July 2002 to reconfirm the line's stability. The line was subsequently named 'SAKCAL097' and its unique characteristics were found to reproduce true to type in successive generations of asexual propagation.

DESCRIPTION OF THE GENUS *CALIBRACHOA* LLAVE & LEX.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida*, the Garden *Petunia,* and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa*, originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

SUMMARY OF THE INVENTION

The following are the most outstanding and distinguishing characteristics of this new cultivar when grown under normal horticultural practices in Kakegawa, Japan.

1. Blue flowers;
2. Large flower size; and
3. Creeping growth habit.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
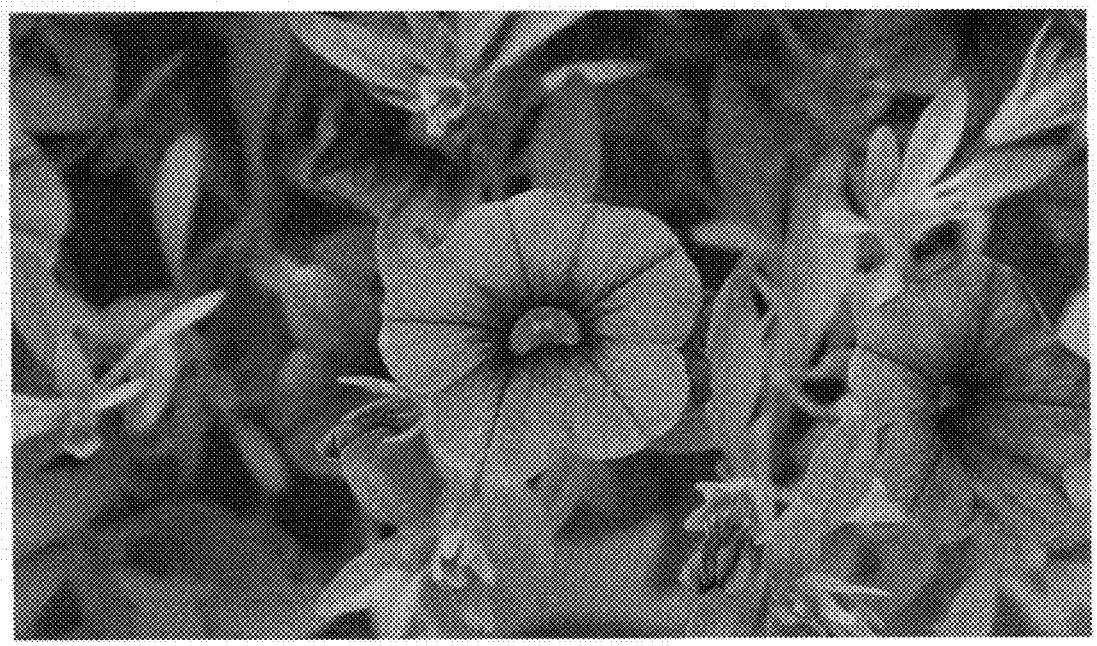

FIG. 2. shows the mature flowers.

DESCRIPTION OF THE NEW CULTIVAR

The following detailed description sets forth the distinctive characteristics of 'SAKCAL097'. The data which define these characteristics were collected from asexual reproductions carried out in Salinas, Calif. The detailed description was taken from plants grown under greenhouse conditions for approximately 4 months from stick date. Color references are to The R.H.S. Colour Chart of The Royal Horticultural Society of London (R.H.S.), 4$^{th}$ Edition.

DETAILED BOTANICAL DESCRIPTION

Classification:

*Family.*—Solanaceae.

*Species.*—*Calibrachoa* sp.

*Common name.*—*Calibrachoa.*

Plant description:

*Life cycle.*—Tender perennial.

*Form.*—Branching.

*Habit.*—Creeping.

*Height* (*from soil line to top of foliage*).—16.0 cm.

*Spread.*—58.0 cm to 60.0 cm.

Propagation:

*Type cuttings.*—Vegetative cuttings.

*Time to produce a rooted cutting.*—6 weeks.

*Time to bloom from propagation.*—10 weeks.

Environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:

*Stem color.*—RHS 144A (Yellow-green).

*Anthocyanin color.*—RHS N187A (Greyed-purple).

*Pubescence.*—Moderate.

*Pubescence color.*—RHS N155A (White).

*Stem description.*—Dull, circular cross-section.

*Stem diameter.*—0.3 cm.

*Stem length.*—30.0 cm to 32.0 cm.

*Internode length.*—3.0 cm to 4.0 cm.

Leaves:

*Arrangement.*—Alternate.

*Shape.*—Elliptic.

*Apex.*—Obtuse.

*Base.*—Attenuate.

*Attachment.*—Decurrant.

*Margin.*—Entire.

*Surface.*—Dull.

*Surface pubescence.*—Slight.

*Pubescence color.*—RHS N155A (White).

*Venation.*—Pinnate.

*Length.*—4.5 cm.

*Width.*—1.5 cm.

*Color.*—Upper surface: RHS 137A (Green). Lower surface: RHS 137B (Green).

*Fragrance.*—Absent.

Flowers:

*Flowering habit.*—Indeterminate.

*Flower type.*—Solitary.

*Flowering requirements.*—Will flower so long as day length is greater than 12 hours and temperature exceeds 13° C.

*Duration of flowers.*—About 5 days.

*Corolla.*—5 petals, fused.

*Corolla shape.*—The flowers are funnel shaped with five fissures and a shallow, yet prominent, indentation of the petal tip at the midvein.

*Fragrance.*—Absent.

Flower buds:

*Surface.*—Pubescent.

*Length.*—2.0 cm to 2.5 cm.

*Diameter.*—0.5 cm to 0.8 cm.

*Shape.*—Ovate.

*Color.*—RHS 79C (Purple) with RHS N187A (Greyed-purple) veins.

*Peduncle.*—Length: 4.0 cm to 4.5 cm. Diameter: 0.1 cm. Color: RHS 144A (Yellow-green). Texture: Moderate pubescence. Appearance: Dull. Pubescence color: RHS N155A (White).

Flower description:

*Flower depth.*—1.0 cm.

*Flower tube length.*—1.5 cm.

*Flower tube diameter.*—1.0 cm.

*Flower diameter.*—4.5 cm to 5.0 cm.

*Calyx.*—5 sepals, free.

*Sepals.*—Shape: Elliptical. Apex: Obtuse. Margin: Entire. Sepal color (both surfaces): RHS 138A (Green).

*Petals.*—Shape: Bilabiate, fused; shallow, yet prominent indentation of the petal tip, mid-vein. Length: 2.0 cm. Width: 2.0 cm. Apex: Truncate. Margin: Entire. Texture: Glabrous.

*Color.* Lobe color: Upper lobe: Closest to RHS N81A (Purple-violet) Lower lobe: Closest to RHS N79D (Purple) with RHS N79A (Purple) veins. Corolla tube color: Inner: RHS 8A (Yellow) with RHS N79A (Purple) veins Outer: RHS 1C (Green-yellow) with RHS 79A (Purple) veins.

*Fragrance.*—Absent.

Reproductive organs:

*Stamen number.*—5, free.

*Stamen color.*—RHS 144D (Yellow-green).

*Pollen color.*—RHS 11A (Yellow).

*Ovary.*—Superior.

*Placenta arrangement.*—Central.

*Pistil number.*—1 (per inflorescence).

*Pistil length.*—1.0 cm.

*Stigma color.*—RHS 144A (Yellow-green).

*Style length.*—0.7 cm.

*Style color.*—RHS 144B (Yellow-green).

Fruit/seed set: No fruit or seeds produced.

Disease and insect resistance: Excellent resistance to rain, heat and drought. Will not tolerate temperature below 10° C. Plants are susceptible to *Botrytis*, powdery mildew, various stem and root rots, and certain viruses, like Tobacco Mosaic Virus and Impatiens Necrotic Spotted Virus. Plants can be infested with aphids, leafminer, whitefly and various *Lepidoptera.*

Comparison with Parental Lines and Known Cultivars

'SAKCAL097' is distinguished from its grandparents mainly by flower color and plant growth habit as shown in Table 1 below.

TABLE 1

| Characteristic | 'SAKCAL097' | Female Grandparent: '0BC-13A' | Male Grandparent: '9B-74AA-1' |
|---|---|---|---|
| Flower color | Blue | Carmine Rose | Violet |
| Plant growth habit | Creeping | Semi-mounding | Creeping |

*Calibrachoa* 'SAKCAL097' is a distinct variety of *Calibrachoa* due to its blue flowers, large flower diameter and creeping growth habit. 'SAKCAL097' is most similar to the variety 'CALTRABLUPU' (U.S. Plant Pat. No. 18,930) however, there are differences in the flower petal color, flower size and plant growth habit as described in the table below (color references are to The Royal Horticultural Society Colour Chart, $4^{th}$ edition):

TABLE 2

| Characteristic | 'SAKCAL097' | 'CALTRABLUPU' |
|---|---|---|
| Petal color, upper surface | Closest to RHS N81A (Purple-Violet) | RHS N81A (Purple-Violet) with circumorbital ring darker than RHS 79A (Purple) and RHS 83A (Purple-Violet) veins |
| Petal color, lower surface | Closest to RHS 79D (Purple) with RHS N79A (Purple) veins | RHS N81C (Purple-Violet) with RHS 83B (Purple-Violet) veins |
| Flower size (diameter) | 4.5-5.0 cm | 3.2 cm |
| Plant growth habit | Creeping | Trialing, outwardly spreading and mounded |

We claim:

1. A new and distinct cultivar of *Calibrachoa* plant as shown and described herein.

* * * * *